US010156625B2

(12) United States Patent
Nehrke et al.

(10) Patent No.: US 10,156,625 B2
(45) Date of Patent: *Dec. 18, 2018

(54) MR IMAGING WITH $B_1$ MAPPING

(71) Applicant: KONINKLIJKE PHILIPS N.V., Eindhoven (NL)

(72) Inventors: Kay Nehrke, Ammersbek (DE); Peter Boernert, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1035 days.

This patent is subject to a terminal disclaimer.

(21) Appl. No.: 14/455,165

(22) Filed: Aug. 8, 2014

(65) Prior Publication Data

US 2015/0042335 A1 Feb. 12, 2015

(30) Foreign Application Priority Data

Aug. 12, 2013 (EP) ..................................... 13180037

(51) Int. Cl.
*G01R 33/565* (2006.01)
*G01R 33/24* (2006.01)
(Continued)

(52) U.S. Cl.
CPC ........ *G01R 33/5659* (2013.01); *A61B 5/0263* (2013.01); *A61B 5/055* (2013.01);
(Continued)

(58) Field of Classification Search
CPC .............. G01R 33/246; G01R 33/5612; G01R 33/5659; G01R 33/56509; A61B 5/055; A61B 5/0263
See application file for complete search history.

(56) References Cited

U.S. PATENT DOCUMENTS 5,303,705 A * 4/1994 Nenov ................. G01R 33/563
600/410
6,653,832 B2 * 11/2003 Wind ................... G01R 33/307
324/307

(Continued)

FOREIGN PATENT DOCUMENTS

WO 2013105006 A1 7/2013

OTHER PUBLICATIONS

Nehrke et al, "Dream-A Novel Approach for Robust, Ultrafast, Multislice B1 Mapping", Magnetic Resonance in Medicine, 2012, vol. 68, p. 1517-1526.

(Continued)

*Primary Examiner* — Dixomara Vargas

(57) ABSTRACT

A method of MR imaging, wherein a portion of a body placed in the examination volume of a MR device is subjected to an imaging sequence of RF pulses and switched magnetic field gradients. The imaging sequence is a stimulated echo sequence including i) at least two preparation RF pulses ($\alpha$) radiated toward the portion of the body during a preparation period, and ii) one or more reading RF pulses ($\beta$) radiated toward the portion of the body during an acquisition period temporally subsequent to the preparation period. One or more FID signals and one or more stimulated echo signals are acquired during the acquisition period. A $B_1$ map indicating the spatial distribution of the RF field of the RF pulses within the portion of the body is derived from the acquired FID and stimulated echo signals.

10 Claims, 2 Drawing Sheets

(51) Int. Cl.
   *G01R 33/561* (2006.01)
   *A61B 5/055* (2006.01)
   *A61B 5/026* (2006.01)

(52) U.S. Cl.
   CPC ....... *G01R 33/246* (2013.01); *G01R 33/5612* (2013.01); *G01R 33/56509* (2013.01)

(56) References Cited

U.S. PATENT DOCUMENTS

| | | | | |
|---|---|---|---|---|
| 6,670,811 | B2* | 12/2003 | Wind | G01R 33/307 324/307 |
| 6,813,513 | B2* | 11/2004 | Goto | G01R 33/56518 324/307 |
| 6,836,115 | B2* | 12/2004 | Wind | G01R 33/307 324/307 |
| 7,941,204 | B1 | 5/2011 | Wang et al. | |
| 8,018,230 | B2* | 9/2011 | Zaitsev | G01R 33/56563 324/309 |
| 8,064,982 | B2* | 11/2011 | Hu | G01R 33/46 324/307 |
| 8,686,727 | B2* | 4/2014 | Reddy | G01R 33/5601 324/307 |
| 9,157,976 | B2* | 10/2015 | Reddy | G01R 33/5605 |
| 2011/0275928 | A1 | 11/2011 | Kim | |
| 2015/0002149 | A1* | 1/2015 | Nehrke | G01R 33/243 324/309 |
| 2015/0253406 | A1* | 9/2015 | Nehrke | G01R 33/246 324/309 |

OTHER PUBLICATIONS

Nehrke et al "Fast B1+ Mapping for Cardiac MR Using a Black Blood Dream Sequence" Proc. Intl. Soc. Mag. Reson. Med 21, Apr. 20, 2013, P. 4271.

Nehrke et al "Volumetric B1+ Mapping of the Brain At 7T Using Dream" Magnetic Resonance in Medicine, Feb. 14, 2013,.

Edelman et al "Fast Selective Black Blood MR Imaging" MR imaging. Radiology. 1991;181:P. 655-660.

\* cited by examiner

MR IMAGING WITH $B_1$ MAPPING

CROSS-REFERENCE TO PRIOR APPLICATIONS

This application claims the benefit European Patent Application No. 13180037.7, filed on Aug. 12, 2013 which is hereby incorporated by reference herein.

FIELD OF THE INVENTION

The invention relates to the field of magnetic resonance (MR) imaging. It concerns methods of MR imaging of at least a portion of a body. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation.

Magnetic resonance angiography (MRA) is a MR imaging technique to visualize blood filled structures, including arteries, veins and the heart chambers. MRA creates soft tissue contrast between blood vessels and surrounding tissues primarily created by flow, rather than displaying the vessel lumen. There are bright blood and black blood MRA techniques, named according to the appearance of the blood vessels. With these different MRA techniques both the blood flow and the condition of the blood vessel walls can be visualized.

SUMMARY OF THE INVENTION

It is generally desirable to have a relatively uniform homogeneity of the generated transmit RF field ($B_1$ field) for excitation of magnetic resonance throughout a cross section and/or a volume of the imaged patient's body. However, as the MR frequency increases, with increasing main magnetic field strength, this becomes more difficult due to conductive losses and wavelength effects within the body of the patient. Consequently, an accurate measurement of the spatial distribution of the transmitted RF field is important for many MR imaging applications to support appropriate prospective (if applicable) and retrospective correction/compensation. This requires a robust and fast $B_1$ mapping technique.

Fast and robust in vivo $B_1$ mapping is an essential pre-requisite for multi-coil transmit applications like RF shimming or accelerated multi-dimensional RF pulses. However, most $B_1$ mapping techniques are relatively slow, making integration into the clinical workflow difficult. This is in particular the case for MRA and, most notably, cardiac $B_1$ mapping, where ECG triggering and breath-holding used to suppress physiological motion further reduces scan efficiency.

From the foregoing it is readily appreciated that there is a need for an improved $B_1$ mapping method which can be applied in MRA and, in particular, in cardiac imaging, where the acquisition of a complete $B_1$ map needs to be performed within a small fraction of a second, thus fitting in the diastolic phase of the heartbeat.

In accordance with the invention, a method of MR imaging of at least a portion of a body placed in the examination volume of a MR device is disclosed. The method comprises the steps of:
  subjecting the portion of the body to a suppression sequence of at least one RF pulse for suppression of MR signals emanating from blood;
  subjecting the portion of the body to an imaging sequence of RF pulses and switched magnetic field gradients, which imaging sequence is a stimulated echo sequence including:

i) at least two preparation RF pulses radiated toward the portion of the body (10) during a preparation period, and ii) one or more reading RF pulses radiated toward the portion of the body during an acquisition period temporally subsequent to the preparation period, acquiring one or more FID signals and one or more stimulated echo signals during the acquisition period; and deriving at least one $B_1$ map indicating the spatial distribution of the RF field of the RF pulses within the portion of the body from the acquired FID and stimulated echo signals.

The recently introduced DREAM $B_1$ mapping approach (Magnetic Resonance in Medicine, 68, 1517-1526, 2012) allows the acquisition of a $B_1$ map in a sufficiently short time interval such that it fits in the diastolic phase of a single heartbeat. However, the stimulated echoes used in the conventional DREAM technique for $B_1$ encoding are sensitive to flow, thereby degrading the $B_1$ maps for the MR signals emanating from the blood pool in the heart chambers. The basic idea of the invention is to combine the DREAM sequence, which serves as an imaging sequence within the meaning of the invention, with a suppression sequence for suppression of MR signals emanating from the blood pool within the imaged region. The suppression sequence may, for example, comprise a black-blood pre-pulse of a per se known kind. In this way, the invention enables in vivo RF shimming in cardiac MR imaging at a main magnetic field strength of 3 Tesla or more.

In accordance with the invention, one or more reading RF pulses are applied during the acquisition period of the stimulated echo sequence, wherein the FID signals and the stimulated echo signals are acquired quasi-simultaneously. A MR image can be reconstructed from the FID signals and another MR image can be reconstructed from the stimulated echo signals. After the MR image reconstruction, the $B_1$ map can be derived from the voxel-wise intensity ratio of the two MR images reconstructed from the FID and stimulated echo signals, respectively.

A plurality of FID signals and stimulated echo signals with appropriate phase encoding need to be acquired for generating a complete $B_1$ map. Efficient sampling schemes like EPI, parallel imaging or compressed sensing can be advantageously applied for this purpose in combination with the invention.

According to a preferred embodiment of the invention, the proposed approach can be used for parallel transmit applications, wherein the RF pulses are radiated toward the portion of the body via two or more RF coils (or two or more sets of RF coils) in parallel. A $B_1$ map may be derived from the acquired FID and stimulated echo signals for each RF coil or set of RF coils, each $B_1$ map indicating the spatial distribution of the RF field of the RF pulses irradiated via the respective RF coil or set of RF coils. In this embodiment of the invention, $B_1$ mapping is performed for multiple RF transmit elements (RF coils) of the used MR device to map their corresponding transmit sensitivities. An individual mapping scan may be performed according to the method of the invention for each individual RF transmit element (or for a combination of them).

The $B_1$ maps obtained according to the invention can advantageously be used in subsequent imaging scans for RF shimming RF shimming refers to the spatial homogenization of the RF transmit field by adjustment of the complex amplitudes of the RF pulses radiated via the individual RF coils of a parallel transmit MR imaging system. Simple known RF shimming approaches use predefined, anatomy-specific RF shim sets, without taking the individual patient anatomy into account. The invention enables a more advanced RF shimming approach, which optimizes the RF shim settings in a patient specific way. For this purpose, one or more $B_1$ maps are derived from the FID and stimulated echo signals in the above-described fashion and optimal RF shim sets are derived from the $B_1$ maps by (per se known) numerical methods.

In case of MR imaging of the thorax (like in cardiac imaging), dynamic changes of the RF field may be expected due to motion (for example breathing motion of the patient), because motion-induced displacements of anatomical structures potentially affect the spatial conductivity and permittivity. Hence, the RF shim settings, derived in a conventional manner for example from a single calibration scan, may degrade, if the subsequent diagnostic MR imaging scan is performed in a different position or motional state of the patient. This can potentially influence the obtained MR images and cause artifacts. The stimulated echo-based $B_1$ mapping technique of the invention allows a $B_1$ map to be acquired in a single shot of the stimulated echo sequence in about 100 ms duration, making the approach in principle real-time capable. In this way, the invention enables dynamic RF shimming, wherein the $B_1$ maps (and the RF shim settings derived therefrom) are updated continuously, for example once per heartbeat. Hence, the RF shimming is performed on the basis of RF shim settings that are automatically adapted to the momentary motional state of the patient. Artifacts due to outdated RF shim settings, like in the prior art, are effectively avoided.

In a preferred embodiment of the invention, a threshold-based masking is applied to the $B_1$ map prior to deriving the RF shim settings. The stimulated echo used by the imaging sequence of the invention is flow-sensitive. Hence, the obtained $B_1$ maps are potentially degraded in the areas affected by flow, for example by blood flow in the chambers and great vessels of the heart, as already explained above. Thus, an appropriate masking of the obtained $B_1$ maps can advantageously be applied. Appropriate image processing may be performed in accordance with the invention to distinguish, for example, blood from myocardium. The suppression sequence achieves a suppression of the blood signal in both the stimulated echo and FID images and thereby allows an automatic, threshold-based masking of the $B_1$ maps. Hence, the areas affected by blood flow are masked when deriving the RF shim settings and sub-optimal RF shimming due to flow artifacts in the $B_1$ maps is effectively avoided.

According to another preferred embodiment of the invention, a plurality of FID and stimulated echo MR signals are generated by means of a plurality of consecutive reading RF pulses, each having a flip angle of less than 90°, preferably less than 45°, most preferably less than 30°. As already mentioned above, a train of reading RF pulses having small flip angles can be used to achieve a fast readout of multiple FID and stimulated echo signals. As short as possible echo times can be used in order to minimize $T_2^*$ relaxation.

According to a further preferred embodiment of the invention, the suppression sequence and/or the imaging sequence are ECG-gated. ECG-gating can be used to trigger the suppression sequence (and the consecutive imaging sequence) such that the FID and stimulated echo signals are acquired after a given time delay after, for example, each R-wave of the ECG signal. In this way, the MR signals can be acquired selectively during the diastolic phase of the heartbeat.

According to yet another preferred embodiment, the suppression sequence comprises at least one black-blood preparation pulse, wherein the imaging sequence is applied after a time delay after the black-blood preparation pre-pulse. With the known so-called black-blood MRA technique flowing blood appears dark. For black-blood preparation, a pair of spatially non-selective and selective 180° inversion RF pulses may be used, followed by a sufficiently long inversion time delay to null MR signal contributions from inflowing blood. Other more sophisticated magnetization preparation pulses may be used in accordance with the invention to further improve the $B_1$ mapping quality.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The methods of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
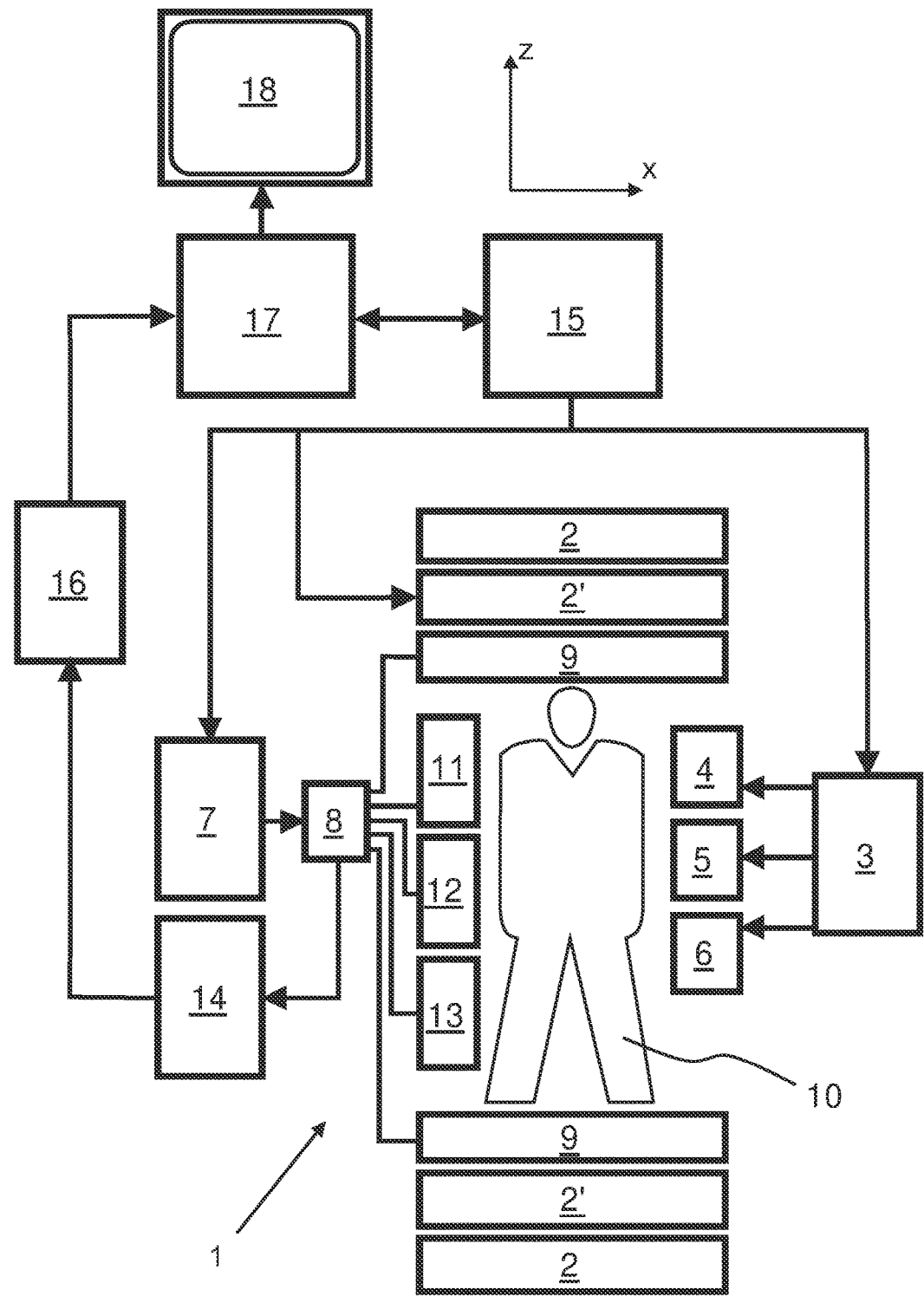
FIG. 1 schematically shows a MR device for carrying out the methods of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions. In parallel transmit applications, the array RF coils 11, 12, 13 may also be used for RF transmission, for example for the purpose of RF shimming. The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
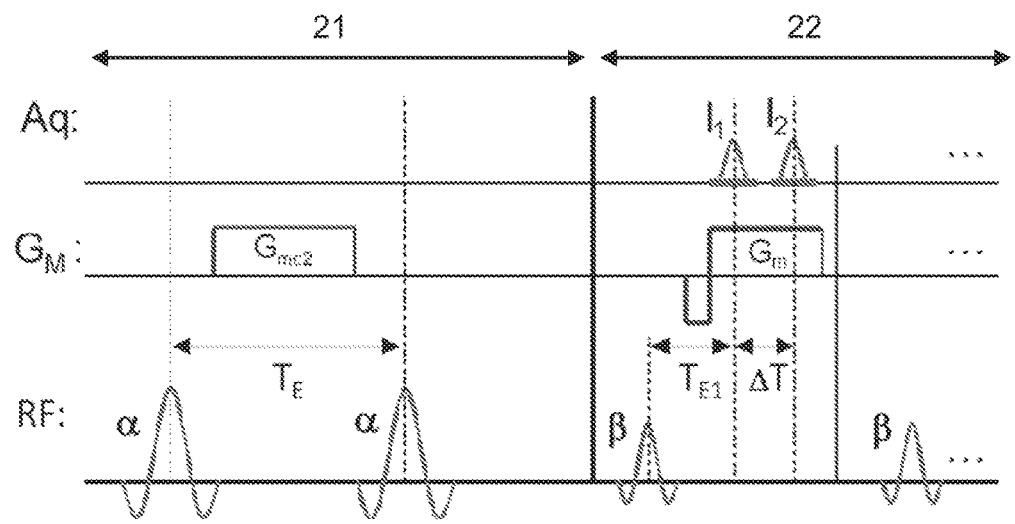
FIG. 2 shows a schematic diagram illustrating an imaging sequence according to the invention.

FIG. 2 shows a diagram illustrating an imaging sequence according to the invention. The depicted imaging sequence is a stimulated echo sequence which is subdivided into a preparation period 21 and an acquisition period 22. Two preparation RF pulses having a flip angle of α are applied during the preparation period 21. The two preparation RF pulses are separated by a time interval $T_E$. A de-phaser magnetic field gradient $G_{mc2}$ is applied between the two preparation RF pulses. A sequence of reading RF pulses having flip-angle β are generated during the acquisition period 22, which is temporally subsequent to the preparation period 21. An FID signal $I_1$ and a stimulated echo signal $I_2$ are acquired after each reading pulse as gradient-recalled echoes.

Directly after the preparation sequence 21, the longitudinal magnetization is given by:

$$M_{z1} = \cos^2(\alpha) \cdot M_0$$
$$M_{z2} = \frac{1}{2}\sin^2(\alpha) \cdot M_0,$$

wherein $M_{z1}$ and $M_{z2}$ denote the un-prepared (i.e. in-phase) and the stimulated echo-prepared (i.e. de-phased) longitudinal magnetization, respectively. In accordance with the invention, both the FID signal $I_1$ generated from $M_{z1}$ and the stimulated echo signal $I_2$ generated from $M_{z2}$ are acquired at different points in time $T_{E1}$ and $T_{E1}+T$, respectively. The delay T between the two echoes $I_1$, $I_2$ is determined by the relation:

$$\Delta T = a_{mc2}/G_m,$$

wherein $A_{mc2}$ denotes the gradient-time area of the de-phaser gradient $G_{mc2}$ and $G_m$ denotes the strength of the readout magnetic field gradient. Neglecting $T_1$- and $T_2$-effects, the two acquired echo signals $I_1$ and $I_2$ are given by:

$$I_1 = S \cdot C(T_{E1})\sin(\beta)M_{z1}$$

$$I_2 = S \cdot C(T_{E1}+\Delta T - T_g)\sin(\beta)M_{s2},$$

wherein S represents a complex system constant, which is equal for both echo signals $I_1$ and $I_2$ and which is determined e.g. by transmit and receive coil sensitivities for a given voxel. β is the nominal flip angle of the reading RF pulses. C describes the static signal de-phasing for a given voxel due to susceptibility and chemical shift effects:

$$C(t) = \int_V \rho(r)e^{-i\omega(r)t}\,dr,$$

wherein ρ and ω denote the proton density and the off-resonance frequency offset, respectively. The integral describes the summation over the given voxel. By applying the timing scheme $$T_E = 2T_{E1} + \Delta T$$

the measured echo signals $I_1$ and $I_2$ are given by:

$$I_1 = S \cdot C(T_{E1})\sin(\beta)M_{z1}$$

$$I_2 = S \cdot C(T_{E1}+\Delta T - T_g)\sin(\beta)M_{s2},$$

Thus, the de-phasing term C is identical for both echo signals, apart from the mirrored phase. For example by selecting $T_{E1}=2.3$ ms at a main magnetic field strength of 3 Tesla, signal contributions from water spins and signal contributions from fat spins are essentially in phase for both echoes $I_1$, $I_2$. Combining the above equations yields:

$$|I_2/I_1| = \tan^2(\alpha)/2$$

Thus, the unknown flip angle of the stimulated echo preparation RF pulses can be derived from the ratio of the acquired echo signals according to:

$$\alpha = \arctan\sqrt{2|I_2/I_1|}$$

It has to be noted that for $B_1$ mapping also the alternative timing scheme $T_E = \Delta T$ can be employed, which results in identical de-phasing terms, i.e. without mirrored phase. However, this variant results in a longer $\Delta T$ and, hence, a longer overall repetition time of the sequence.

The imaging sequence shown in FIG. 2 is actually a basic version of the known DREAM $B_1$ mapping sequence (Magnetic Resonance in Medicine, 68, 1517-1526, 2012).

Figure 3:
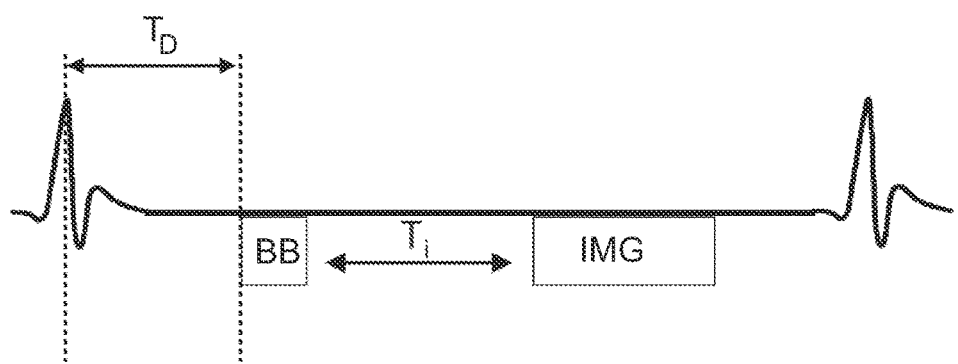
FIG. 3 shows a timing diagram illustrating the combination of the imaging sequence with a black-blood preparation pre-pulse applied according to the invention within the diastolic phase of a single heartbeat.

FIG. 3 shows a schematic diagram illustrating the application of the DREAM imaging sequence IMG as illustrated in FIG. 2 in combination with a suppression sequence, which is a black-blood preparation pulse BB in the depicted embodiment, the black-blood preparation pulse BB being radiated prior to the imaging sequence in order to suppress contributions from blood spins to the FID and stimulated echo signals $I_1$, $I_2$. The time interval $T_i$ between the black blood sequence BB and the imaging sequence is adjusted to approximately null the blood signal contribution to the stimulated echo and FID signals $I_1$, $I_2$ underlying the $B_1$ maps. Other magnetization preparation pulses may be added to further improve the $B_1$ mapping quality.

The generation of the black-blood preparation pulse BB (and consequently also the generation of the imaging sequence IMG) is ECG-triggered. The time delay $T_D$ is selected to acquire the stimulated echo and FID signals $I_1$, $I_2$ in the diastolic phase of the heartbeat.

The RF pulses of the imaging sequence IMG are radiated toward the body 10 in parallel via the RF coils 11, 12, 13, wherein the obtained $B_1$ maps indicate the spatial distribution of the RF field of the RF pulses radiated via the respective RF coils 11, 12, 13. The $B_1$ maps are employed for RF shimming RF shim settings are derived from the $B_1$ maps, wherein the amplitudes and phases of the RF pulses are controlled according to the RF shim settings for each RF coil 11, 12, 13 in order to achieve an optimum homogeneous distribution of the $B_1$ field within the imaged region. In order to avoid flow-artifacts, the obtained $B_1$ maps used for computing the RF shim settings are masked automatically using a simple threshold applied to the MR images reconstructed from the FID and stimulated echo signals $I_1$, $I_2$ respectively.

The approach of the invention allows a two-dimensional $B_1$ map to be acquired in a single heart beat, which makes it possible to integrate the sequence into the clinical workflow of a parallel transmit MR imaging system, as described above. $B_1$ maps may be acquired for several slices, orientations, and/or transmit channels in clinically acceptable breath hold durations. The proposed magnetization preparation-based blood suppression scheme facilitates masking of the blood pool signal, thus improving the accuracy of the $B_1$ maps and, hence, the quality of RF shimming, considering only reliable $B_1$ estimates.

More advanced black-blood preparation pulses suitable for multi-slice excitation could be employed in a straight forward manner, further increasing the flexibility of the approach.

The invention claimed is:

1. Method of MR imaging of at least a portion of a body placed in the examination volume of a MR device, the method comprising the steps of:
    subjecting the portion of the body to a suppression sequence of at least one RF pulse for suppression of MR signals emanating from blood;
    subjecting the portion of the body to an imaging sequence of RF pulses and switched magnetic field gradients, which imaging sequence is a stimulated echo sequence including:

i) at least two preparation RF pulses radiated toward the portion of the body during a preparation period, and
ii) one or more reading RF pulses radiated toward the portion of the body during an acquisition period temporally subsequent to the preparation period,
acquiring one or more FID signals and one or more stimulated echo signals during the acquisition period; and
deriving at least one $B_1$ map indicating the spatial distribution of the RF field of the RF pulses within the portion of the body from the acquired FID and stimulated echo signals.

2. Method of claim 1, wherein the $B_1$ map is derived from the voxel-wise intensity ratio of the FID and stimulated echo signals.

3. Method of claim 1, wherein the RF pulses are radiated toward the portion of the body via two or more RF coils, wherein the $B_1$ map indicates the spatial distribution of the RF field of the RF pulses radiated via the two or more RF coils.

4. Method of claim 3, wherein RF shim settings are derived from the $B_1$ map, wherein the amplitudes and phases of the RF pulses radiated toward the portion of the body via the two or more RF coils are controlled according to the RF shim settings.

5. Method of claim 4, wherein a threshold-based masking is applied to the $B_1$ map prior to deriving the RF shim settings.

6. Method of claim 1, wherein a plurality of FID and stimulated echo MR signals are generated by means of a plurality of consecutive reading RF pulses.

7. Method of claim 1, wherein the suppression sequence and/or the imaging sequence are ECG-gated.

8. Method of claim 1, wherein the suppression sequence comprises at least one black-blood preparation pre-pulse, wherein the imaging sequence is applied after a time delay after the black-blood saturation pre-pulse.

9. MR device comprising at least one main magnet coil for generating a uniform, steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals, wherein the MR device is arranged to perform the following steps:
    subjecting the portion of the body to a suppression sequence of at least one RF pulse for suppression of MR signals emanating from blood;
    subjecting the portion of the body to an imaging sequence of RF pulses and switched magnetic field gradients, which imaging sequence is a stimulated echo sequence including:
    i) at least two preparation RF pulses radiated toward the portion of the body during a preparation period, and
    ii) one or more reading RF pulses radiated toward the portion of the body during an acquisition period temporally subsequent to the preparation period,
    acquiring one or more FID signals and one or more stimulated echo signals during the acquisition period; and
    deriving at least one $B_1$ map indicating the spatial distribution of the RF field of the RF pulses within the portion of the body from the acquired FID and stimulated echo signals.

10. Computer program to be run on a MR device, which computer program comprises instructions for:
    generating a suppression sequence of at least one RF pulse for suppression of MR signals emanating from blood;
    generating an imaging sequence of RF pulses and switched magnetic field gradients, which imaging sequence is a stimulated echo sequence including:
    i) at least two preparation RF pulses radiated during a preparation period, and
    ii) one or more reading RF pulses radiated during an acquisition period temporally subsequent to the preparation period,
    acquiring one or more FID signals and one or more stimulated echo signals during the acquisition period; and
    deriving at least one $B_1$ map indicating the spatial distribution of the RF field of the RF pulses from the acquired FID and stimulated echo signals.

* * * * *